United States Patent [19]

Ohtsuru et al.

[11] Patent Number: 4,822,928

[45] Date of Patent: Apr. 18, 1989

[54] PROCESS FOR PRODUCING 2,5-DICHLOROTOLUENE

[75] Inventors: Masashi Ohtsuru, Tokyo; Toshio Hozumi, Iwaki, both of Japan

[73] Assignee: Kureha Kagaku Kogyo Kabushiki Kaisha, Tokyo, Japan

[21] Appl. No.: 81,072

[22] Filed: Aug. 3, 1987

[30] Foreign Application Priority Data

Aug. 5, 1986 [JP] Japan .................. 61-183644

[51] Int. Cl.$^4$ .............. C07C 17/33; C07C 17/22; C07C 21/24

[52] U.S. Cl. .................... 570/190; 570/209; 570/210

[58] Field of Search ............ 570/190, 209, 210

[56] References Cited

U.S. PATENT DOCUMENTS

| | | | |
|---|---|---|---|
| 4,010,214 | 3/1977 | Gelfand | 570/209 |
| 4,031,146 | 6/1977 | Di Bella | 260/650 R |
| 4,059,642 | 11/1977 | Dewald et al. | 570/190 |
| 4,269,674 | 5/1981 | Osa et al. | 204/81 |
| 4,329,524 | 5/1982 | Dewald | 570/190 |

FOREIGN PATENT DOCUMENTS

| | | | |
|---|---|---|---|
| 3617137 | 11/1986 | Fed. Rep. of Germany . | |
| 26485 | 7/1971 | Japan | 570/210 |
| 1036234 | 2/1986 | Japan | 570/190 |
| 529147 | 12/1976 | U.S.S.R. | 570/210 |
| 1490677 | 11/1976 | United Kingdom . | |

OTHER PUBLICATIONS

Silberrad, "J. Chem. Soc." (1925) pp. 2677–2684.
Chemical Abstracts, vol. 104, No. 7, p. 496, Abstract No. 50631t (1986).
USSN 863601 (Pending) (Equivalent to West German Patent Above According to Applicant).

*Primary Examiner*—J. E. Evans
*Attorney, Agent, or Firm*—Nixon & Vanderhye

[57] ABSTRACT

Disclosed herein is a process for producing 2,5-dichlorotoluene which is useful as a monomer of heat-resistant polymers and an intermediate raw material for medicines, agricultrual chemicals and various organic synthetic substances, the process giving 2,5-dichlorotoluene at a high selectivity and in a high yield and comprising the steps of chlorinating 4-t-alkyltoluene or 4-isopropyltoluene in the presence of a catalyst, thereby obtaining a 2,5-dichlorocompound, and bringing the formed 2,5-dichlorocompound into contact with toluene in the presence of a catalyst, thereby subjecting the 2,5-dichlorocompound to transalkylation.

8 Claims, No Drawings

PROCESS FOR PRODUCING 2,5-DICHLOROTOLUENE

BACKGROUND OF THE INVENTION

The present invention relates to a process for producing 2,5-dichlorotoluene which is used as a monomer in the production of heat-resistant polymers represented by polyether sulfone, polyether ketone, polyphenylene sulfide, etc. and can be used as a raw material for various organic synthetic chemical substances, for example, medicines and agricultural chemicals.

The present invention also relates to a specific process for producing 2,5-dichlorotoluene in a favorable yield, in spite of the difficulty obtaining 2,5-dichlorotoluene by ordinary chlorination of toluene.

It has been known that various isomers are formed when dichlorotoluene is produced by chlorinating toluene. Namely, since a methyl group possessed by toluene and a chlorine atom which is to be introduced into toluene nucleus by chlorination are the ortho-para orientating groups and the methyl group shows a stronger ortho-para orientation, when toluene is chlorinated to obtain dichlorotoluene, both 2,4-dichlorotoluene and 2,6-dichlorotoluene are easily formed, however, 2,5-dichlorotoluene is relatively seldom formed.

Accordingly, various processes have been proposed so as to produce 2,5-dichlorotoluene. For instance, one prior process involves the preliminary formation of 2-chlorotoluene and then, in step, of introducing the second chlorine atom into 2-chlorotouene, by bringing 0.5 to 0.9 molecule of chlorine into reaction per molecule of 2-chlorotoluene in the presence of a metal catalyst accompanying a sulfur compound as a co-catalyst (see, U.S. Pat. No. 4,031,146). However, in this process, the reaction rate of 2-chlorotoluene must be controlled and sufficiently low, i.e. 50 to 70%, in order to suppress the formation of trichlorotoluene by product in amounts less than 6%, and as a result, there is a problem that the yield of 2,5-dichlorotoluene is inevitably low (the yield being 30 to 42%).

Another process is known whereby 0.9 to 1.1 molecules of chlorine are brought into reaction per molecule of 2-chlorotoluene in the presence of sulfur and/or a sulfur compound as a catalyst (see, Japanese Patent Application Laid-Ooen (Kokai) No. 51-143627/1976). However, in this process, although the yield of 2,5-dichlorotoluene is improved to 50%, there is a problem, on the other hand, that by-production of trichlorotoluene increases to 8%.

Still more, among the processes using 2-chlorotoluene as a starting material, a process of bringing 1.0 to 1.6 molecules of chlorine into reaction per molecule of 2-chlorotoluene while using iodine as a catalyst has been known (refer to Japanese Patent Application Laid-Open (Kokai) No. 57-91934/1982). In this process, although the yield of 2,5-dichlorotoluene is as high as 53%, there is still a problem that as much as 14 to 22% of trichlorotoluene is formed as a by-product.

Moreover, other than these processes, a process of chlorinating 2-chlorotoluene using L-type zeolite as a catalyst has been proposed. However, the selectivity of forming 2,5-dichlorotoluene of the process is only around 56% and a by-production of trichlorotoluene is unavoidable.

As has been described above, all the processes already known are not yet satisfiable for producing 2,5-dichlorotoluene at a high selectivity and in a high yield.

The present invention overcomes many of the problem associated with prior processes described above and thus is capable of producing 2,5-dichlorotoluene at a high selectivity and in a high yield. It has been found that these advantages can be attained by the preliminary introduction of a specified group at the para-position of toluene, chlorinating the treated toluene under specified conditions, and then subjecting the chlorinated compound to transalkylation together with toluene.

SUMMARY OF THE INVENTION

An object of the present invention is to provide a process for producing 2,5-dichlorotoluene which can be used as a monomer of for heat-resistant polymeric substances such as polyether sulfone, polyether ketone, polyphenylene sulfide, etc. and as an intermediate raw material or various organic synthetic chemical substances including medicines and agricultural chemicals.

Furthermore, another object of the present invention is to provide a special process for producing 2,5-dichlorotoluene at high selectivity and in high yield, in spite of the difficulties encountered when 2,5-dichlorotoluene is formed by ordinary chlorination of toluene.

DETAILED DESCRIPTION OF THE INVENTION

The present invention is embodied in a process whereby 2,5-dichlorotoluene is obtained by chlorinating 4-t-alkyltoluene or 4-isopropyltoluene at room temperature to a temperature of 80° C. in the presence of a Friedel-Crafts catalyst and sulfur or a sulfur-containing compound or in the presence of iron (II) and/or (III) sulfide, thereby obtaining a 2,5-dichloro-4-t-alkyltoluene or 2,5-dichloro-4-isopropyltoluene without substantially forming trichlorotoluene, and then bringing the obtained 2,5-dichloro-4-t-alkyltoluene or 2,5-dichloro-4-isopropyltoluene into contact with toluene in the presence of a Friedel-Crafts catalyst, thereby effecting transalkylation. 4-t-alkyltoluene or 4-isopropyltoluene is used as the starting material for the chlorination reaction. However, from a commercial production of viewpoint the preferred starting material is 4-t-butyltoluene or 4-isopropyltoluene.

That is, 4-t-alkyltoluene or 4-isopropyltoluene, which is obtained by conventional alkylation of toluene, for instance, a reaction of toluene with t-alkyl chloride or propylene, is preferably used as a starting material and 2,5-dichloro-4-t-alkyltoluene or 2,5-dichloro-4-isopropyltoluene is produced by chlorinating the starting material in the presence of a Friedel-Crafts catalyst and sulfur or poorer sulfur-containing compound or in the presence of iron (II) and/or (III) sulfide, thereby introducing chlorine atoms to 2- and 5-positions of the starting material. The reaction for obtaining 2,5-dichloro-4-t-alkyltoluene or 2,5-dichloro-4-isopropyltoluene can be carried out at a room temperature to a temperature of 80° C., preferably 40° to 60° C. while bringing gaseous chlorine into reaction with the starting material keeping the degree of chlorination between 2 and 2.2 (the degree of chlorination means the molar amount of chlorine reacted with one molecule of the starting material and is measured by the remaining amount of supplied chlorine in the ordinary reaction system and the theoretical amount of chlorine, or is measured by the gaschromatographic method). In these cases, when the reaction temperature is over 80° C., by-production of other dichloro-4-t-alkyl or isopropyltoluene, for instance, 2,6-dichloro-4-t-alkyl or isopropyltoluene and 2,3-dichloro-4-t-alkyl or isopropyltoluene, as well as that of 4-t-alkyl or isopropyl trichlorotoluene, etc. increase. On the other hand, when the reaction temperature is lower than room temperature, poorer reaction efficiency and the selectivity result. By the term "selectivity" is meant the rate of formation of 2,5-dichlorotoluene in all the dichlorotoluene derivatives formed in the reaction.

As the Friedel-Crafts catalyst, anhydrous ferric chloride, anhydrous aluminum chloride, anhydrous antimony (III) chloride and anhydrous antimony (V) chloride may be exemplified and such a catalyst is used together with sulfur or a sulfur-containing compound. As the sulfur-containing compound used herein, the compounds represented by the following formulae (I), (II) and (III) can be mentioned:

$$R^3-S-R^4 \quad (I)$$

$$R^3-(S)_n-R^4 \quad (II)$$

and $$R^3-SH \quad (III)$$

(wherein $R^3$ and $R^4$ represent respectively an alkyl group, an aryl group, a cycloalkyl group or a heterocyclic group and may be same or different from each other and n is an integer of 2 to 8), such as dodecyl sulfide, diphenyl sulfide, diphenyl disulfide, tetrahydrothiophene, thiophene, cyclohexylmercaptan, benzenethiols and mixtures of more than two of them.

Furthermore, other than the case of using Friedel-Crafts catalyst together with the sulfur-containing compound, iron sulfide only can be used for the purpose.

The amount of Friedel-Crafts catalyst used according to the present invention is 0.01 to 0.1, preferably 0.01 to 0.08 molecule per one molecule of the starting material, for instance, 4-isopropyltoluene. The amount of sulfur or the sulfur-containing compound used is 0.01 to 1.0 time, preferably 0.01 to 0.8 times by weight of the amount of Friedel-Crafts catalyst used. Further, in the case of using iron (II) and/or (III) sulfide only, the amount thereof is 0.001 to 0.1, preferably 0.001 to 0.01 molecule to one molecule of the starting material.

According to the present invention, after ending the chlorination reaction, the catalyst is removed from the reaction mixture and the reaction mixture is then subjected to distillation for recycling the unreacted starting material and monochloro derivatives of alkylated toluene to the chlorination reaction. Thereafter, 2,5-dichloro-4-t-alkyltoluene or 2,5-dichloro-4-isopropyltoluene is separated from the distillation residue. The yield of the 2,5-dichloro-4-t-alkyl or isopropyltoluene is about 70% and the selectivity thereof is more than 90%.

In the next step, the obtained 2,5-dichloro-4-t-alkyltoluene or 2,5-dichloro-4-isopropyltoluene is brought into contact with toluene, thereby subjecting to transalkylation, disconnecting the t-alkyl group or the isopropyl group from the mother compound to obtain 2,5-dichlorotoluene.

In the reaction of the transalkylation, the 2,5-dichlorocompound (2,5-dichloro-4-t-alkyltoluene or 2,5-dichloro-4-isopropyltoluene) can be treated in an excess amount of toluene at 20° to 60° C., preferably 25° to 35° C. for 4 to 5 hours in the presence of Friedel-Crafts catalyst. Toluene to be used is in an amount of not smaller than 2 times, preferably 10 to 20 times by volume of the 2,5-dichlorocompound. It should be noted that when toluene is used in an amount of less than 2 times of 2,5-dichlorocompound, the object reaction does not proceed and when using too much amount of toluene, it is uneconomical from the view point of separating the product after the reaction.

Further, since when the reaction temperature is over 60° C., the yield of 2,5-dichlorotoluene is reduced accompanying the by-production of colored substances, it is not desirable.

Moreover, the amount of Friedel-Crafts catalyst used in transalkylation is preferably 0.01 to 3.0, more preferably 0.01 to 1.0 molecule per one molecule of the raw material, 2,5-dichlorocompound.

After the transalkylation reaction is over, the catalyst is removed from the reaction mixture by washing with water and distilling the remaining oil layer, the object product, 2,5-dichlorotoluene is obtained, while 4-t-alkyltoluene or 4-isopropyltoluene is obtained as the by-product.

The yield of 2,5-dichlorotoluene is not smaller than 90% and each of the by-products is obtained in a yield of not smaller than 90%.

Accordingly, in the present invention, these by-products obtained by the transalkylation can be recycled and reused as the starting material for the chlorination reaction.

As has been described, since in the present invention, a 4-t-alkyltoluene or 4-isopropyltoluene is used as the starting material and by transalkylating a 2,5-dichloro-4-t-alkyltoluene or 2,5-dichloro-4-isopropyltoluene obtained by chlorinating the starting material, 2,5-dichlorotoluene can be produced in a high yield and in the same time, the starting material can be recovered in a high yield and reused, the process of the present invention can be an extremely profitable commercial process.

The present invention will be explained more concretely while referring to the non-limitative Examples as follows.

EXAMPLE 1

Chlorination for obtaining 2,5-dichloro-4-t-butyltoluene

After adding 3.3 g (0.020 mol) of anhydrous ferric chloride ($FeCl_3$) and 1.5 g (0.047 mol) of sulfur (a simple substance), as the catalyst, to 296 g (2.0 mol) of 4-t-butyltoluene, gaseous chlorine was blown into the mixture kept at about 45° C. at a rate of 40 liters per hour to carry out chlorination of 4-t-butyltoluene until the degree of chlorination reached 2.1. Then, the obtained liquid reaction mixture was washed with water to remove the catalyst and after drying the organic layer with anhydrous sodium sulfate, the dried organic layer was distilled to recover unreacted 4-t-butyltoluene and monochlorinated substance in the first distillate for reuse in the step of chlorination and the next distillate of boiling point of 70° to 75° C./0.5 mmHg, namely, 2,5-dichloro-4-t-butyltoluene of a purity of not less than 93% was collected in a yield of 75%.

Transalkylation of 2,5-dichloro-4-t-butyltoluene

After adding a large excess of 2000 g of toluene and 64 g (0.48 mol) of anhydrous aluminum chloride, as a catalyst, to 284 g (1.3 mol) of 2,5-dichloro-4-t-butyltoluene obtained as stated above, the mixture was brought into reaction for 5 hours at room temperature under a vigorous agitation thereof.

After washing the obtained liquid reaction mixture by water to remove the catalyst, the organic layer was distilled to obtain 2,5-dichlorotoluene and 4-t-butyltoluene respectively in a quantitative yield. The obtained 4-t-butyltoluene was recovered and reused in the chlorination step.

EXAMPLE 2

Step of chlorination

After adding 3.3 g (0.020 mol) of anhydrous ferric chloride (FeCl₃) and 1.5 g (0.047 mol) of sulfur (a single substance), as catalysts, to 264 g (2.0 mol) of 4-isopropyltoluene, gaseous chlorine was blown into the mixture at a temperature of 45° C. at a rate of 40 liters/hour to carry out chlorination until the degree of chlorination reached 2.1. After the chlorination was over, the liquid reaction mixture was washed with water to remove the catalyst and after drying the organic layer with anhydrous sodium sulfate, the dried organic layer was distilled. After recovering unreacted 4-isopropyltoluene and monochlorinated substance as the first distillate, a fraction of boiling point of 68° to 70° C./0.5 mmHg, of a purity of 97% and in a yield of 75% was obtained as 2,5-dichloro-4-isopropyltoluene.

Step of transalkylation

After adding 2000 g of toluene to 267 g (1.3 mol) of 2,5-dichloro-4-isopropyltoluene obtained and further adding 64 g (0.48 mol) of anhydrous aluminum chloride, as a catalyst, the mixture was kept at room temperature and the newly formed mixture was brought into reaction for 5 hours under a vigorous agitation.

After washing the liquid reaction mixture with water to remove the catalyst, the organic layer was distilled to obtain 190 g of 2,5-dichlorotoluene and 168 g of 4-isopropyltoluene.

EXAMPLE 3

In the same manner as in Example 1 except for carrying out chlorination while using 0.9 g of iron (II) sulfide (FeS) as a catalyst instead of using anhydrous ferric chloride and sulfur in Example 1, 193 g of 2,5-dichlorotoluene were obtained.

What is claimed is:

1. A process for producing 2,5-dichlorotoluene, which process comprises the steps of chlorinating a 4-t-alkyltoluene or 4-isopropyltoluene at room temperature to a temperature of 80° C. in the presence of a Friedel-Crafts catalyst and sulfur or a sulfur-containing compound or in the presence of iron sulfide to obtain a 2,5-dichloro-4-t-alkyltoluene or 2,5-dichloro-4-isopropyltoluene without substantially forming trichlorotoluenes, and of bringing the obtained 2,5-dichloro-4-t-alkyltoluene or 2,5-dichloro-4-isopropyltoluene into contact with toluene in the presence of a Friedel-Crafts catalyst, thereby effecting transalkylation on the 2,5-dichloro-4-t-alkyltoluene or 2,5-dichloro-4-isopropyltoluene.

2. A process according to claim 1, wherein said chlorination step is carried out at a temperature of from 40° to 60° C.

3. A process according to claim 1, wherein said transalkylation is carried out at a temperature of from 20° to 60° C. while using toluene of not less than 2 times by volume of 2,5-dichloro-4-t-alkyltoluene or 2,5-dichloro-4-isopropyltoluene.

4. A process according to claim 1, wherein gaseous chlorine is brought into reaction with 4-t-alkyltoluene or 4-isopropyltoluene in said chlorination step to the extent that the degree of chlorination is to be kept at the value between 2 to 2.2.

5. A process according to claim 1, wherein said Friedel-Crafts catalyst is one selected from the group consisting of anhydrous ferric chloride, anhydrous aluminum chloride, anhydrous antimony (III) chloride, anhydrous antimony (V) chloride and a mixture thereof.

6. A process according to claim 1, wherein said sulfur-containing compound is either of the compound represented by the formulae (I), (II) and (III) or a mixture thereof:

(I),

(II)

and

(III)

wherein $R^3$ and $R^4$ represent respectively an alkyl group, an aryl group, a cycloalkyl group or a heterocyclic group and may be the same or different from each other and n is an integer of from 2 to 8.

7. A process according to claim 1, wherein said sulfur-containing compound is one selected from the group consisting of dodecyl sulfide, diphenyl sulfide, diphenyl disulfide, tetrahydrothiophene, cyclohexylmercaptan and a mixture thereof.

8. A process according to claim 1, wherein 4-t-alkyltoluene or 4-isopropyltoluene obtained at said step of transalkylation as a by-product is used as the starting material for said step of chlorinating thereof.

* * * * *